US007097997B1

(12) United States Patent
Deslys et al.

(10) Patent No.: US 7,097,997 B1
(45) Date of Patent: Aug. 29, 2006

(54) METHOD FOR DIAGNOSING A TRANSMISSIBLE SPONGIFORM SUBACUTE ENCEPHALYOPATHY CAUSED BY AN UNCONVENTIONAL TRANSMISSIBLE AGENT STRAIN IN A BIOLOGICAL SAMPLE

(75) Inventors: Jean-Philippe Deslys, Le Chesnay (FR); Emmanuel Comoy, Le Plessis-Robinson (FR); Jacques Grassi, Bures-sur-Yvette (FR)

(73) Assignee: Commissariat a l'Energie Atomique, Paris (FR)

( * ) Notice: Subject to any disclaimer, the term of this patent is extended or adjusted under 35 U.S.C. 154(b) by 303 days.

(21) Appl. No.: 10/129,111

(22) PCT Filed: Nov. 13, 2000

(86) PCT No.: PCT/FR00/03159

§ 371 (c)(1),
(2), (4) Date: Aug. 22, 2002

(87) PCT Pub. No.: WO01/35104

PCT Pub. Date: May 17, 2001

(30) Foreign Application Priority Data

Nov. 12, 1999 (FR) .................................. 99 14242

(51) Int. Cl.
*C12Q 1/37* (2006.01)
*A01N 37/18* (2006.01)
*A61K 38/00* (2006.01)

(52) U.S. Cl. ............................. 435/23; 514/2; 514/15; 514/16

(58) Field of Classification Search .................... 514/2, 514/15–16; 435/23
See application file for complete search history.

(56) References Cited

U.S. PATENT DOCUMENTS

| | | | | |
|---|---|---|---|---|
| 5,733,734 A * | 3/1998 | Trojanowski et al. | ........ | 435/7.1 |
| 5,773,253 A * | 6/1998 | Linsley et al. | ............. | 435/69.7 |
| 5,876,712 A * | 3/1999 | Cheever et al. | ............ | 424/93.7 |
| 5,877,012 A * | 3/1999 | Estruch et al. | ........... | 435/252.3 |

FOREIGN PATENT DOCUMENTS

| | | |
|---|---|---|
| EP | 0 861 900 | 9/1998 |
| JP | 10 267928 | 10/1998 |
| WO | 98 30909 | 7/1998 |
| WO | 99 41280 | 8/1999 |
| WO | WO 9941280 A1 * | 8/1999 |
| WO | 99 66956 | 12/1999 |
| WO | 00 22438 | 4/2000 |
| WO | 00 26238 | 5/2000 |
| WO | 00 29849 | 5/2000 |
| WO | 00 29850 | 5/2000 |

OTHER PUBLICATIONS

Viles, et al. Copper Binding to the Prion Protein: Structural Implications of Four Identical Cooperative Binding Sites, Proc. Natl Acad. Sci. USA, vol. 96, Mar. 1999, pp. 2042-2047.*
Lehmann, et al., Two Mutant Prion Proteins Expressed in Cultured Cells Acquire Biochemical Properties Reminiscent of the Scrapie Isoform, Proc. Natl. Acad. Sci. USA, vol. 93, May 1996, pp. 5610-5614.*
Oesch, et al. A Cellular Gene Encodes Scrapie PrP 27-30 Protein, Cell, vol. 40, Apr. 1985, pp. 735-746.*
Sequence Information Center, http:ww.life.uiuc.edu/z-huang/sequences.html, printed Aug. 5, 2004, pp. 1-14.*
Dual Epitope Recognition By the BASP EVH1 Domain Modulates Polyproline Ligand Specificity and Binding Affinity, The Embo Journal, vol. 19, No. 18, 2000, pp. 4903-1914.*
NCBI Conserved Domain Database, http:///www.ncbi.hlm.gov/Structure/ccd/ccdsrv/cgi?uid=pfam01857.*
Cesareni, et al., Cn we infer peptide recognition specificity mediated by SH3 domains?, FEBS Letters, vol. 513, Issue 1, 2002 pp. 38-44.*
Preliminary Report, the Evaluation of Tests for the Diagnosis of Transmissible Spongiform Encephalopathy in Bovines, European Commission, Directorate-General XXIV, Jul. 8, 1999, pp. 1-36.*
Rudolf K. Meyer et al.: "Detection of bovine spongiform encephalopathy-specific PrPSc by treatment with heat and guanidine thiocyanate" Journal of Virology, vol. 73, No. 11, pp. 9386-9392, Nov. 1999.
Simone Hornemann et al.: "A scrapie-like unfolding intermediate of the prion protein domain PrP (121-231) induced by acidic pH" Proceedings of the National Academy of Sciences of the United States, vol. 95, No. 11, pp. 6010-6014, May 26, 1998.
S. Krasemann et al.: "Induction of antibodies against human prion proteins (PrP) by DNA-mediated immunization of PrPmice" Journal of Immunological Methods, vol. 199, No. 2, p. 117, Dec. 15, 1996.

* cited by examiner

*Primary Examiner*—Christopher Tate
*Assistant Examiner*—Jennifer Ione Harle
(74) *Attorney, Agent, or Firm*—Oblon, Spivak, McClelland, Maier & Neustadt, P.C.

(57) ABSTRACT

The invention relates to a method for diagnosing a transmissible spongiform subacute encephalopathy (TSSE) caused by an unconventional transmissible agent (UTA) or prion. The method involves treating a sample suspected of containing a prion with proteinase K for a time and under conditions that completely degrade normal prion protein (Prp-sen), but which only partially digest abnormal prion protein (PrP-res) so that all or some of the octapeptide motif repeats comprising P(H/Q)GGG(-/T)WGQ (SEQ ID NO: 1) in the abnormal prion protein (Prp-res) are retained.

18 Claims, 13 Drawing Sheets
(1 of 13 Drawing Sheet(s) Filed in Color)

Influence of the composition of the buffers for the differential detection of BSE and scrapie.

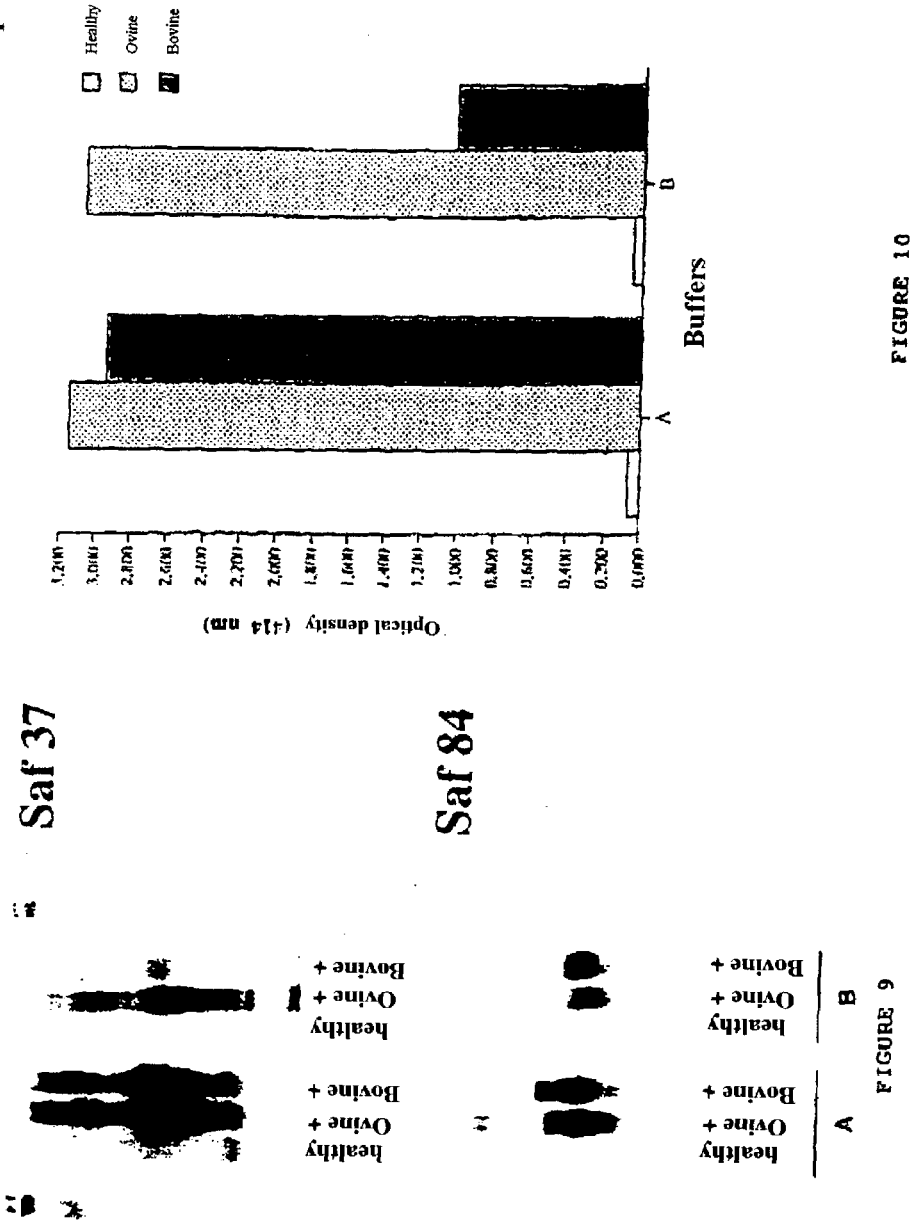

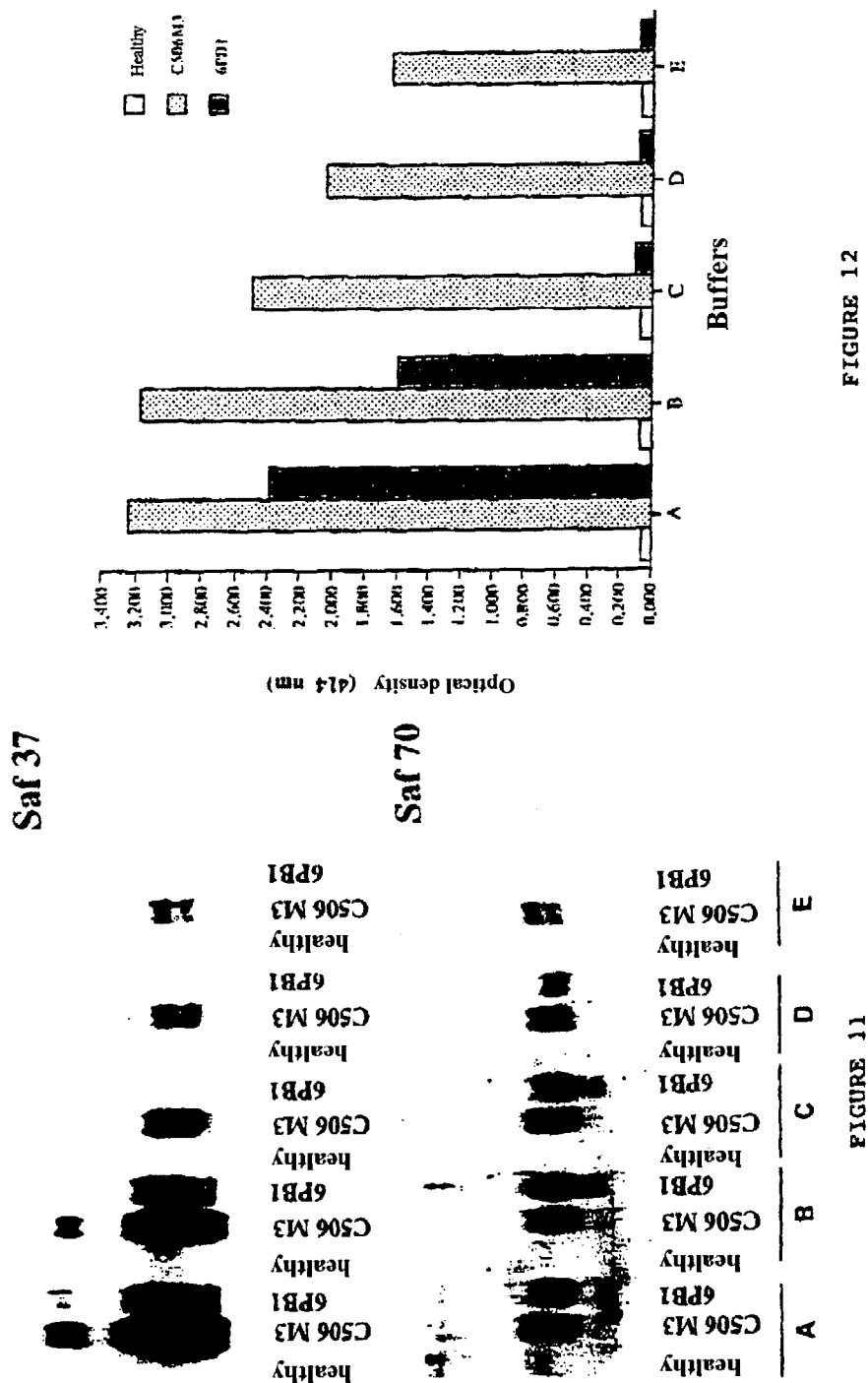

Influence of the composition of the buffers and of the proteinase K concentration for the detection of the various types of CJD

Direct digestion of brain homogenates
with proteinase K
Saf 37
Healthy
Type 1
Type 2
Type 3
Type 4
Antibody directed against
region 94-230 of the PrP
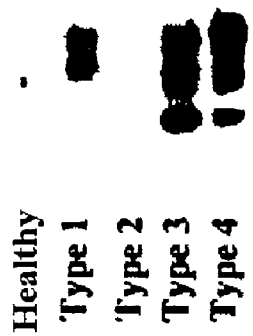
Healthy
Type 1
Type 2
Type 3
Type 4
FIGURE 15

Differences in resistance of the PrP-res to proteinase K as a function of the types of CJD

FIGURE 16

METHOD FOR DIAGNOSING A TRANSMISSIBLE SPONGIFORM SUBACUTE ENCEPHALYOPATHY CAUSED BY AN UNCONVENTIONAL TRANSMISSIBLE AGENT STRAIN IN A BIOLOGICAL SAMPLE

BACKGROUND OF THE INVENTION

1. Field of the Invention

The present invention relates to a method for diagnosing a TSSE caused by a UTA strain, in a biological sample, by detecting PrP-res, and also to the use thereof in the context of differential diagnosis of the various UTA strains in a biological sample.

2. Description of Background Art

Transmissible spongiform subacute encephalopathies (TSSEs) are caused by unconventional transmissible agents (UTAs), also called prions, the precise nature of which to date remains disputed. TSSEs essentially comprise Creutzfeldt-Jakob disease in humans (CJD), scrapie in sheep and goats, and bovine spongiform encephalopathy (BSE) in bovines. Other encephalopathies have been demonstrated in the Felidae, in mink or certain wild animals, such as deer or elk.

These diseases are always fatal and, at the current time, there is no effective treatment.

In TSSEs, there is an accumulation of a host's protein, PrP (or prion protein), in an abnormal form (PrP-res), mainly in the central nervous system; PrP-res copurified with infectiousness and accumulation thereof precedes the appearance of histological lesions. In vitro, it is toxic for cultures of neurons.

The two isoforms of PrP have the same amino acid sequence (see FIG. 1), but are different in their secondary structure: PrP-res has a significantly higher content of β-pleated sheets, whereas normal PrP (PrP-sen) has a greater number of α-helices.

Two biochemical properties make it possible, in general, to distinguish these two isoforms.

PrP-res is partially resistant to proteases, in particular to proteinase K (PK), which causes cleavage of its N-terminal end. After the action of PK, PrP-res is often called PrP27-30 because of the apparent molecular weight of the diglycosylated form; it is generally accepted that the cleavage site of PrP-res is located between amino acids 89 and 90 (Prusiner et al, Cell, 1984) for conventional strains.

PrP-res is insoluble in nonionic detergents, such as Triton X100 or Triton 114.

The normal form of the prion protein (PrP-sen) is, in principle, completely degraded by proteases and is entirely soluble in the presence of nonionic detergents.

The peptide sequences of hamster, human, bovine and ovine PrP-sen are presented in FIG. 1; they comprise, in particular, an octapeptide motif P(H/Q)GGG(-/T)WGQ (SEQ ID NO: 1), repeated 4 or 5 times, depending on the species. This octapeptide motif repeat corresponds to amino acids 51–91 of the PrP (numbering of the sequence of the human PrP) (B. Oesch et al., 1991).

For detecting the presence of the infectious agent, the most recent methods are based on selective detection of the abnormal PrP (PrP-res) linked to the infectious agent, by taking advantage of its partial resistance to proteases.

It is possible to distinguish:

Western blotting methods which are based on the immunological detection of PrP-res in a tissue extract, after treatment of the extract with a protease so as to destroy the normal isoform of the PrP (PrP-sen), separation of the proteins of the extract by electrophoresis, transfer onto a polymer membrane, and detection with a specific antibody which recognizes the PrP (Schaller O. et al., 1999), tests of the ELISA type, which also involve treating tissue extract with a protease.

Among these various tests, which involve treating the tissue extracts with a protease, mention may be made of:

that described by Serban et al. (Neurology, 1990, 40, 110), who has developed a test for detecting PrP-res which includes immobilization of the proteins on a nitrocellulose membrane, followed by protease digestion, denaturation and immunodetection with monoclonal antibodies.

that described by Oesch et al. (Biochemistry, 1994, 33, 5926–5931), who have proposed, to quantify the amount of PrP-res, an immunofiltration assay for purifying PrP-res (ELIFA or enzyme-linked immunofiltration assay).

that described by Gratwohl et al., 1997, who propose an assay of the ELISA type. After treatment of the samples with proteinase K and purification of PrP-res by centrifugation, the latter is adsorbed onto microtitration plates and detected using rabbit polyclonal antibodies.

that described by Safar et al., 1998, who does not use proteinase K but compares the immunoreactivity of PrP-res immobilized on a solid support depending on whether or not it has been subjected to denaturing treatment.

In general, these various tests have the drawback of lacking sensitivity and thus of causing false-negatives.

Other methods propose treating the sample with denaturing products (Oesch et al., 1994 and 1999; WO 00/22438, The Reagents of the University of California), a limited treatment with proteinase K (WO 00/29850, Wallac Oy et al.) or treatment with a metallopeptidase (WO 00/22438), which make hidden antigenic sites accessible, which sites can be detected with the monoclonal antibody 3F4 which recognizes region 109–112 of PrP (WO 00/29850 or WO 00/22438).

The method described in WO 00/29850, Wallac Oy et al., has the major drawback of lacking specificity, due, in particular, to incomplete elimination of PrP-sen under the recommended treatment conditions, while the method described in WO 00/22438, The Regents of the University of California, lacks sensitivity due to the use of the detecting antibody 3F4 (WO 00/22438), which binds to only one motif on the protein.

The applicant has recently provided a test for the quantitative detection of PrP-res, which comprises a purification step which leads to significantly more sensitive detection and which represents a great advance for medical monitoring and assaying PrP-res in abattoirs. This method is, in particular, described in PCT international application WO 99/41280 and in a preliminary report of Directorate General XXIV of the European Commission (consumer policy and consumer health protection; http://europa.eu.int/comm/dg24/health/).

However, given the need for a particularly reliable test for diagnosing TSSEs, the applicant has continued its studies.

BRIEF SUMMARY OF ASPECTS OF THE INVENTION

It has in particular established that, in order to produce a detection test:

(i) which is sensitive, i.e. which has the ability to correctly identify uninfected animals, (ii) which is specific, i.e. which has the ability to correctly identify infected animals exhibiting clinical symptoms, (iii) which has as low a detection limit as possible, i.e. which can allow detection of small amounts of PrP-res (detection of PrP-res before the appearance of clinical symptoms), and (iv) which is reproducible, the biological sample to be analyzed must be treated under conditions which make it possible to conserve all or some of the octapeptide motifs exclusively in PrP-res.

It has been found in particular that, in order to effectively satisfy the four conditions (i)–(iv) stated above, it is necessary to define precise conditions for treating the sample to be analyzed, which completely eliminate PrP-sen from the sample, while at the same time allowing specific capture of PrP-res, under the defined conditions.

DETAILED DESCRIPTION OF THE PREFERRED EMBODIMENTS

A subject of the present invention is a method for diagnosing (method A) a TSSE or prion disease caused by a UTA strain, by detecting PrP-res in a biological sample characterized in that it comprises:

(1) treating said sample with at least one proteinase K (PK) in such a way as to completely degrade PrP-sen while at the same time conserving all or some of the octapeptide motif repeats of PrP-res, whatever the UTA strain; preferably, said PK treatment is carried out at a concentration of between 30 μg/ml and 200 μg/ml for 10 minutes at 37° C. for a homogenate at 10% (biological sample in the form of a homogenate in a suitable buffer), or for a period and at a concentration which are equivalent to the concentration of between 30 μg/ml and 200 μg/ml for 10 minutes at 37° C. for a homogenate at 10%.

(2) bringing said treated sample into contact with a ligand for said octapeptide motifs, in particular antibodies directed against said octapeptide motif repeats, and (3) detecting the possible presence of the octapeptide motif repeats/ligand complex.

According to an advantageous embodiment of the method, the treatment with said proteinase K is between 30 seconds and 2 hours, at a temperature of less than 80° C., preferably between 10 minutes and 30 minutes at 37° C., at the abovementioned concentrations, and even more preferably for 10 minutes at a concentration of between 30 μg/ml and 200 μg/ml for a homogenate at 10% (final concentration) or for 30 minutes at a concentration of between 10 μg/ml and 70 μg/ml for a homogenate at 10% (final concentration) or at a concentration of between 25 μg/ml and at 175 μg/ml for a homogenate at 25% (final concentration).

It should be noted a certain number of parameters are closely related to one another: the concentration of proteinase K depends directly on the duration of treatment (incubation time) of the sample; it may be considered that, at 37° C. for example, a 10 minute incubation with a PK at a concentration of between 30 and 200 μg/ml of homogenate at 10% is equivalent to a 30 minute incubation with a PK at a concentration of between 10 and 70 μg/ml of homogenate at 10%. For example, an incubation for 30 minutes with a PK at 25 μg/ml is equivalent to a 10 minute incubation with a PK at a concentration of 75 μg/ml.

Whatever the concentration of PK and the duration of incubation, the sample treated should no longer contain undegraded PrP-sen, whereas PrP-res, possibly present, has conserved all or some of the octapeptide motifs.

Other parameters may be involved, to a lesser degree, (i.e. in a nonessential way) in establishing the active concentration of PK: this involves, in particular, the buffer in which said PK is dissolved; when the PK is dissolved in the sample homogenization buffer, depending on the homogenization buffer used, the minimum concentration of PK may vary within the range of concentrations specified above:

in a glucose buffer or in guanidine (or a salt thereof), the minimum concentration of PK is preferably 25 μg/ml (incubation for 30 minutes) or 75 μg/ml (incubation for 10 minutes);

in PBS buffer, the minimum concentration of PK is preferably 50 μg/ml (incubation for 30 minutes) or 150 μg/ml (incubation for 10 minutes).

Advantageously, the PK can be used in a buffer which is different from the homogenization buffer; such a buffer advantageously comprises at least one surfactant and/or at least one chaotropic agent and/or at least one salt.

Also advantageously, after treatment (or incubation) of the sample with proteinase K, the suspension obtained is advantageously treated under the conditions defined in international application 99/41280, namely:

addition to said suspension of a buffer B, as defined in that international application 99/41280, and in particular $C_3$–$C_6$ alcohols and mixtures of alcohol, the mean theoretical dielectric constant of which is between 10 and 25, centrifugation of the suspension obtained and solubilization of the pellet in a buffer comprising at least one surfactant and/or at least one chaotropic agent, under the conditions defined in said international application 99/41280.

Such has test has the advantage of being particularly suitable for the differential diagnosis of the TSSEs in the same host, caused by various UTA strains, and in particular for the differential diagnosis of BSE strains compared to the conventional strains of scrapie in sheep.

It has, for example, been shown that the BSE strain has infected humans in Great Britain, by analyzing the electrophoretic profiles of the the PrP-res, which has shown differences in migration depending on the UTA strains; a characteristic profile (type 4) has been found in patients who develop a new variant of Creutzfeld-Jacob disease (vCJD), which appears to be linked to the passing of cattle infected with the BSE agent into human food (Collinge et al., Nature, 1996). A similar profile has been observed in a macaque infected with the BSE agent (Lasmezas et al., 1996) and a cat probably contaminated with this agent (Priola et al., Nature Med., 1996).

However, it is a long method which is tricky to implement if reproducible results are desired, which probably constitutes an element of the controversy which exists regarding the classification of the various types of PrP-res and the use of this method (Parchi et al., Nature, 1997).

There is also a strong suspicion of contamination of sheep with the BSE agent (Butler, Nature, 1998). These animals are in fact sensitive to this agent, although among ovines, there exists an endemic disease, scrapie, another TSSE, which has close and undifferentiatable clinical and histological characteristics. The only reference method for differential diagnosis between the BSE agent and the scrapie agent is inoculating mice and studying the lesional profile, which necessitates a wait of approximately two years, and which has been performed in Great Britain only on 9 sheep for a population of several tens of millions of heads of sheep.

First attempts have been made to try to distinguish the various UTA strains in a sample; Kuczius T. et al., 1999, had considered that the variations observed between the various TSSE strains (scrapie, BSE and CJD) using the glycotyping technique do not make it possible to distinguish each strain; they have selected other biochemical and biological markers for PrP-res which make it possible to distinguish the various prion strains from one another more clearly. The analytical parameters which they have used are as follows: long-term resistance to proteinase K, molecular mass of the PrP-res, topology and amount of the deposits of PrP-res. The results obtained show that the PrPs-res of various strains of BSE and of scrapie exhibit significant differences in their long-term resistance to proteinase K. The resistance to PK varies depending on the strain of scrapie: low resistance: Chandler strain; intermediate resistance: 22A strain; relative stability: 87V strain. Under the same conditions, the BSE strains exhibit intermediate resistance. Although glycotyping does not make it possible to distinguish between scrapie strain 87V and the BSE strains, these two types of strains are clearly distinguishable after long-term treatment with PK. However, these are not protocols which are sufficiently reliable and which can be used on a large scale and in the field.

In this context, it is important to have a reliable, sensitive method for detecting PrP-res which allows differential diagnosis, is relatively inexpensive and easy to carry out, using a biological sample, such as a tissue sample.

Consequently, a subject of the present invention is also a method for the differential diagnosis (method B) of TSSEs caused by UTA strains, in a biological sample, by detecting the PrPs-res associated with the various UTA strains, characterized in that it comprises:

(a) detecting PrP-res in a first fraction of said sample, in accordance with steps (1) to (3) of the method for diagnosing a UTA strain as defined above (method A), and then:

(b) for each sample for which the presence of an octapeptide motif repeats/ligand complex is detected in step (a):

treating a second fraction of said sample with at least one proteinase K (PK) in such a way that the majority of the octapeptide motif repeats are eliminated for the PrP-res associated with at least one strain of interest, in particular the BSE strain, and such that all of the PrPs-res associated with the other UTA strains conserve all or some of said octapeptide motif repeats, under said conditions; preferably, said treatment is carried out under the same conditions as those defined in step (1) or (a), but at a concentration of PK higher than that used in step (1) or (a), bringing said second fraction of said sample treated into contact with a ligand capable of specifically recognizing said octapeptide motif repeats, and detecting the possible presence of the octapeptide motif repeats/ligand complex.

A subject of the present invention is also a method for the differential diagnosis (variant of method B) of TSSEs caused by UTA strains, in a biological sample considered to contain PrP-res (detection tests carried out by any method), characterized in that it comprises, for each sample for which the presence of a PrP-res has been detected:

treating another fraction of said biological sample in accordance with step b) as defined above,
bringing said second fraction of said sample treated into contact with a ligand capable of specifically recognizing said octapeptide motif repeats, and
detecting the possible presence of the octapeptide motif repeats/ligand complex.

In the context of the differential diagnosis (method B), besides the concentration of PK, other conditions may possibly have an effect on the degradation of the octapeptide motifs, depending on the strain: specifically, when the PK is used in a buffer which is different from the homogenization buffer, such as a buffer which advantageously comprises at least one surfactant and/or at least one chaotropic agent and/or at least one salt, the number of octapeptide motifs degraded may vary depending on the composition of said buffer and on the concentration of the various agents.

The term "strain of interest" is intended to mean the UTA strain(s), in particular the BSE strain, for which the intention is to eliminate the octapeptide motif repeats, for example.

One of the main characteristics of methods A and B is to exploit the conditions under which the protease treatment is carried out, so as to control the degradation of the octapeptide motif repeats. Depending on the use envisaged, the method will be carried out such that these motifs are conserved (method A) or destroyed (method B):

in the context of method A, the aim of this control will be to conserve all or some of the octapeptide motif repeats for the purpose of promoting very sensitive detection of PrP-res;

in the context of method B, the aim of controlling the degradation by the protease will be to degrade the majority, and optionally all, of the octapeptide motif repeats for the PrPs-res corresponding to the strain(s) of interest, whatever the species in which it (they) is (are) expressed, under conditions in which all or some of the octapeptide motif repeats are conserved for the PrPs-res corresponding to all the other TSSE strains. In this case, the advantage of the invention is to allow differential diagnosis of the strain of interest relative to the other UTA strains.

Specifically:

Surprisingly, under the conditions according to step (1) or step (a), the PK does not lead to the cleavage of all or some of the octapeptide motif repeats of the PrPs-res associated with all UTA strains or prions, whereas the conditions of step (b) lead to the cleavage of the octapeptide motif repeats of the PrP-res associated with the strain of interest, while all the PrPs-res associated with the other UTA strains conserve all or some of said octapeptide motif repeats.

Also surprisingly, such a test, in particular when the ligand is an antibody, has the following advantages:

great sensitivity of detection since the antibodies directed against these octapeptide motif repeats have a much greater affinity than the antibodies directed against other regions of the PrP-res 27-30 and are more resistant to the buffers used; specifically, the recognition of a repeat motif promotes interactions of high affinity and provides the possibility of attaching several antibody molecules to a single PrP molecule;

the possibility of differential diagnosis of the UTA strains or prions since it is possible, depending on the conditions used, to obtain or not to obtain digestion of these motifs; it is in particular possible to eliminate them for all the diseases linked to the strain of interest, the agent for BSE for example, whereas it is possible to conserve it for the other "prion" diseases. As a result of this, the methods according to the invention provide a simple test for the differential diagnosis of BSE and/or of another strain of interest, relative to the other strains, by using two different conditions (step (1) or (a) and step (b)), the conditions of step (1) or (a) (conserving the octapeptide motif repeats of the PrPs-res associated with all UTA strains) allowing the detection of all the strains, and the conditions of step (b) (eliminating these motifs only in the PrP-res associated with a strain of interest) revealing only the other strains.

Such tests therefore in particular find an application in the investigation of the contamination of sheep with the BSE strain, which is not usually possible to distinguish from the conventional strains of scrapie.

According to an advantageous embodiment of said methods, the PK is dissolved in a buffer which preferably comprises:

a. at least one surfactant, selected from the group consisting of:

anionic surfactants, such as SDS (sodium dodecyl sulfate), sarkosyl (lauroylsarcosine), sodium cholate, sodium deoxycholate or sodium taurocholate;

zwitterionic surfactants, such as SB 3-10 (decylsulfobetaine), SB 3-12 (dodecylsulfobetaine), SB 3-14, SB 3-16 (hexadecylsulfobetaine), CHAPS and deoxy-CHAPS;

nonionic surfactants, such as C12E8 (dodecyl-octaethylene glycol), Triton X100, Triton X114, Tween 20, Tween 80, MEGA 9 (nonanoylmethylglucamine), octylglucoside, LDAO (dodecyldimethylamine oxide) or NP40, or mixtures of surfactants, such as a mixture of an ionic surfactant and a nonionic surfactant, a mixture of two ionic surfactants or a mixture of an ionic surfactant and a zwitterionic surfactant, and/or b. at least one chaotropic agent, selected from the group consisting of urea and guanidine, or a mixture thereof, and/or c. at least one salt selected from the salts of metals which may or may not be alkali metals.

According to an advantageous arrangement of this embodiment, said buffer comprises at least 5% of anionic surfactant, preferably sarkosyl, optionally combined with SDS.

According to another advantageous embodiment of said methods, the ligand is selected from the group consisting of aptamers and antibodies capable of binding specifically to the region of the octapeptide motif repeats.

A subject of the present invention is also a diagnostic kit for carrying out the methods according to the invention, characterized in that it comprises, in combination, at least one surfactant and/or at least one chaotropic agent and/or at least one salt and a protease, as defined above.

The octapeptide motif repeats/antibody complex (when the ligand is an antibody) is detected by standard immunological methods.

BRIEF DESCRIPTION OF THE DRAWINGS

The patent or application file contains at least one drawing executed in color. Copies of this patent or patent application publication with color drawing(s) will be provided by the office upon request and payment of the necessary fee.

Besides the above arrangements, the invention also comprises other arrangements which will emerge from the following description, which refers to examples of implementation of the method which is the subject of the present invention and also to the appended drawings, in which:

FIGS. 7–12 illustrate the influence of the buffers in the differential detection of BSE and of scrapie.

FIG. 15 illustrates the results obtained with direct digestion of brain homogenates using proteinase K.

FIG. 16 illustrates the differences in resistance of the PrP-res to proteinase K as a function of the types of CJD.

Figure 1:
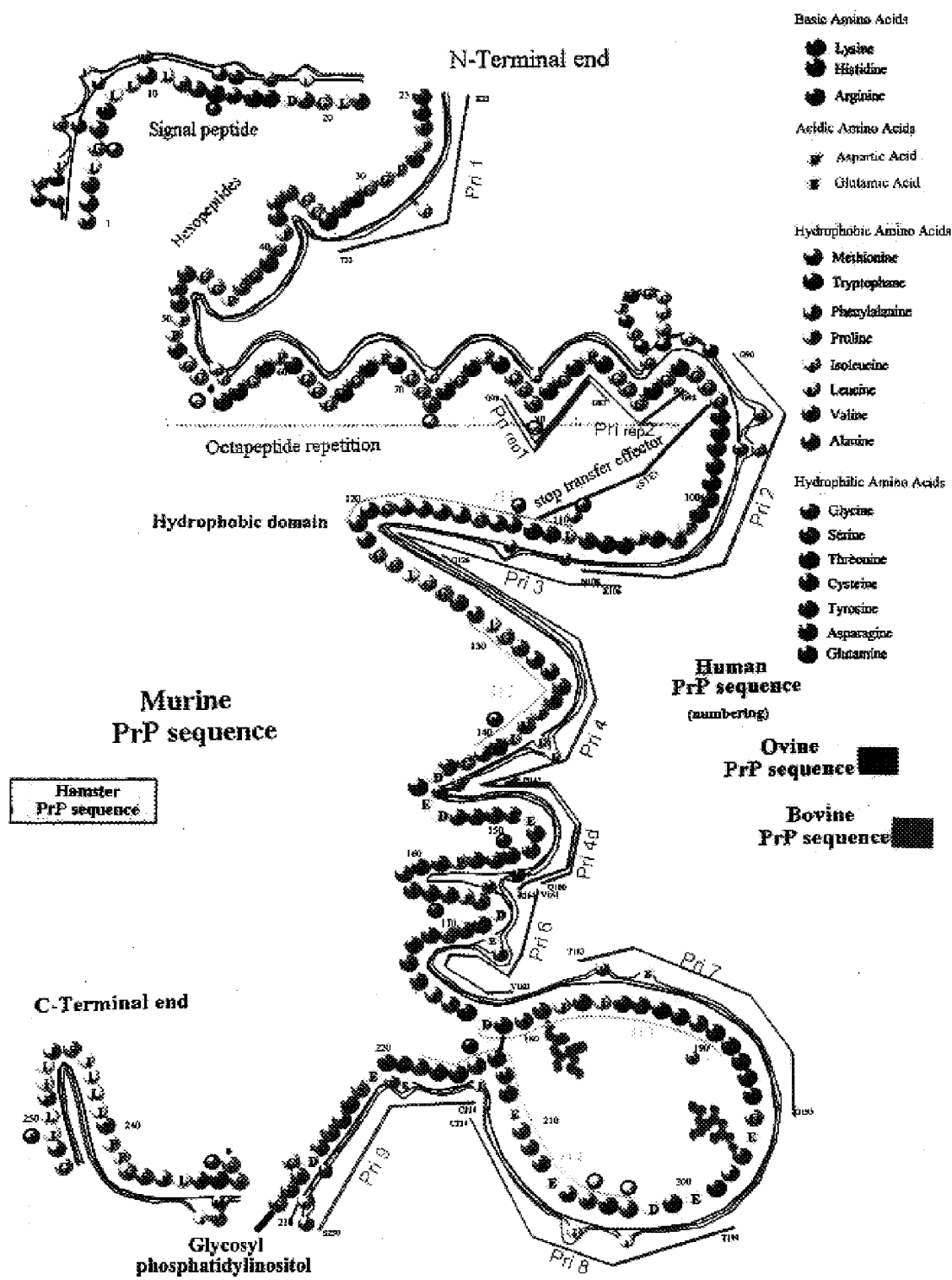
FIG. 1 represents the various PrP sequences: human, ovine, bovine, murine and of the Cricetidae.

It should be clearly understood, however, that these examples are given only by way of illustration of the subject of the invention, of which they in no way constitute a limitation.

EXAMPLE 1

Production and Characterization of Monoclonal Antibodies Specific for the Octapeptide Motif Repeat Synthesis and Labeling of the Peptide A peptide representative of the PrP octapeptide motif repeat, for example the motif G-G-W-G-Q-P-H-G-G-G-W-G-Q-G-$_{(NH2)}$, corresponding to sequence 79–92 of the human PrP, was synthesized using an automatic synthesizer (Milligen 9050, Waters, Milford, Mich.). The peptide was covalently coupled to acetylcholinesterase (AchE) via a heterobifunctional reagent, succinimidyl 4-(N-male-imidomethyl)cyclohexane-1-carboxlate (SMCC, Calbiochem, France), as described previously for other peptides or proteins (McLaughlin et al., 1987, Grassi et al., 1989). This method involves reacting a thiol group introduced into the peptide with the maleimide function which was attached to the AchE by reaction with the SMCC. The thiol group was introduced into the peptide by reaction with N-succinimidyl S-acetylthioacetate (SATA) as described previously (McLaughlin et al., 1987). Coupling was obtained by reacting the AchE-SMCC with an excess of thiolated peptide.

Immunization and Preparation of Monoclonal Antibodies

A preparation of scrapie-associated fibrils (SAFs, PrP-res preparation) was obtained from infected hamster brains (263K scrapie strain) as described previously (Lasmezas et al., 1997). This preparation was inactivated by treatment with formic acid, before immunization of the mice. PrP knockout mice (in which the PrP gene has been eliminated) (PrP$^{0/0}$ mice) were immunized with these SAF preparations and hybridoma cells were prepared as previously described (Grassi et al., 1988, 1989). The culture supernatants were screened as described above. It was possible to identify and stabilize 57 hybridomas; they were named SAF-1 to SAF-90. All these antibodies proved to recognize the SAFs immobilized on the microtitration plates, while a minority of them demonstrated an ability to recognize peptide-AchE conjugates. Among the latter, seven clearly recognize the octapeptide motif repeat (peptide 79–92); they are the antibodies SAF-15, SAF-31, SAF-32, SAF-33, SAF-34, SAF-35 and SAF-37. The list of antibodies obtained, and also the main characteristics thereof, are given in the table below. After cloning and expansion in the form of ascites fluid, the monoclonal antibodies were purified by affinity chromatography on a protein A-sepharose column and stored at −20° C. until use. The isotype of the antibody was determined by radial immunodiffusuion according to the Ouchterlony technique.

Screening of Hybridoma Culture Supernatants

The presence of a PrP-specific antibody in the hybridoma culture supernatants was demonstrated in two ways, by testing their ability to bind either peptide-AchE conjugates or hamster SAFs. In the first case, the screening was performed in plates containing an anti-mouse IgG antibody immobilized as previously described (Créminon et al., 1993, Frobert et al., 1991). In summary, 100 µl of culture supernatants and 100 µl of peptide-AchE conjugate were reacted overnight at +4° C. in plates containing immobilized goat anti-mouse IgG antibodies. After the plates had been washed, 200 µl of Ellman reagent (Ellman et al., 1961) were added to the wells in order to detect the presence of AchE attached to the solid phase. In the second case, plates containing an immobilized SAF preparation were prepared by reacting 50 µl of a 2 µg/ml solution in a 0.05 M phosphate buffer, pH 7.4, overnight at room temperature. After washing, the plates were saturated with the EIA buffer (100 mM phosphate buffer, pH 7.4, containing 150 mM NaCl, 0.1% of bovine serum albumin (BSA) and 0.01% sodium azide) overnight at +4° C. and were kept at this temperature until they were used. The binding of the monoclonal antibodies to the immobilized SAFs was revealed using goat anti-mouse IgG antibodies labeled with AchE as previously described (Negroni et al., 1998).

TABLE

Monoclonal antibodies produced against a preparation of hamster SAF

| Mabs | Isotype | Peptide recognized |
| --- | --- | --- |
| SAF 1 | IgM | X |
| SAF 2 | ? | A |
| SAF 3 | IgG2a | X |
| SAF 4 | IgG2a | A |
| SAF 5 | IgG1 | X |
| SAF 7 | IgG2a | X |
| SAF 8 | IgG1 | A |
| SAF 9 | IgG1 | A |
| SAF 10 | IgG1 | A |
| SAF 11 | IgG2a | X |
| SAF 12 | IgM | A |
| SAF 13 | IgM | A |
| SAF 14 | IgG1 | A |
| SAF 15* | IgG3 | 79–92 |
| SAF 21 | IgG1 | X |
| SAF 22 | ? | A |
| SAF 23 | IgG1 | X |
| SAF 24 | IgG1 | A |
| SAF 31* | IgG2b | 79–92 |
| SAF 32* | IgG2b | 79–92 |
| SAF 33* | IgG2b | 79–92 |
| SAF 34* | IgG2a | 79–92 |
| SAF 35* | IgG2b | 79–92 |
| SAF 37* | IgG2b | 79–92 |
| SAF 42 | IgG1 | A |
| SAF 44 | IgM | A |
| SAF 50 | IgM | A |
| SAF 51 | IgM | A |
| SAF 53* | IgG2a | X |
| SAF 54* | IgG2b | 142–160 |
| SAF 56 | IgM | A |
| SAF 58 | IgM | A |
| SAF 59 | IgM | A |
| SAF 60* | IgG2b | 142–160 |
| SAF 61 | IgG2a | 142–160 |
| SAF 63 | IgM | A |
| SAF 65 | IgG1 (?) | A |
| SAF 66 | IgG2a | 142–160 |
| SAF 67 | IgG1 | X |
| SAF 68 | IgG2a | X |
| SAF 69* | IgG2b | 142–160 |
| SAF 70* | IgG2b | 142–160 |
| SAF 72 | IgG2b | A |
| SAF 73 | IgG1 | X |
| SAF 75 | IgG2a | 142–160 |
| SAF 76 | IgG2a | 142–160 |
| SAF 77 | IgG1 | X |
| SAF 80 | IgG1 | X |
| SAF 81* | IgM | A |
| SAF 82 | IgG1 | A |
| SAF 83* | IgG1 | A |
| SAF 84* | IgG2b | A |
| SAF 85 | IgM | A |
| SAF 91 | IgM | A |
| SAF 94 | IgM | A |
| SAF 95 | IgG1 | A |
| SAF 96 | IgM | A |

79–92: antibodies which recognize the peptide 79–92
142–160: antibodies which recognize the peptide 142–160
Epitope X: antibodies which do not recognize the immobilized SAFs
Epitope A: antibodies which recognize the peptide 126–164 but do not bind the peptide 142–160.
*monoclonal antibodies which demonstrated their ability to recognize the PrP-sen of at least one species tested during this study (human, bovine, ovine, mouse or hamster) in the context of an immunometric assay.

EXAMPLE 2

Detection of PrP-res by Western Blotting

I: Treatment of the Sample (i) Preparation of a Tissue Homogenate from the Various Biological Samples cow BSE, sheep scrapie, human vCJD (type 4), human sporadic CJD (type 1) and corresponding negative controls 350 mg of bovine brain are taken: it is ground and homogenized at 20% (w/v) in a 5% glucose solution.

To perform the homogenization, the brain sample (350 mg) and 1.4 ml of glucose solution are introduced into tubes comprising ceramic beads, and vigorously agitated (Hybaid Ribolyser).

The positive samples were diluted in a homogenate originating from healthy brains of the corresponding species, as follows:

for sheep: to 1/100th for cows: to 1/50th for humans: type 1 or 4: to 1/40th; type 3: to 1/80th; type 2: to 1/20th (ii) Conditions for Step (I)

A first fraction (500 µl) of homogenate at 20% obtained in (i) is incubated with 500 µl of a buffer comprising 10% sarkosyl (SK10), 10% Triton X100 (T10), 2M urea (U2) and proteinase K (PK) at 60 µg/ml of buffer (PK1), for 10 minutes at 37° C. (corresponding to a final concentration of 30 µg/ml for a homogenate at 10%).

In FIGS. 3–6, PK3 corresponds to a concentration of PK of 180 µg/ml of buffer, and PK6 corresponds to a concentration of PK of 360 µg/ml of buffer.

(iii) 500 μl of a buffer consisting of 1-butanol (corresponding to buffers B, as described in international application WO 99/41280) are added; the mixture is centrifuged at 15 000 rpm for 5 min (approximately 17 000 g).

(iv) The centrifugation pellet, which contains the PrP-res, is taken up in 80–100 μl of a buffer C as described in international application WO 99/41280, preferably a Laemmli buffer containing 4% of SDS, and heated at 100° C. for 5 min, in order to carry out Western blotting, or taken up successively in a buffer C1 comprising 6M urea and 0.5% sarkosyl, followed by heating for 5 min at 100° C., and then in a buffer C2 comprising 2M guanidine, followed by heating for 5 min at 100° C., in order to perform an immunometric assay.

(v) Conditions for Step (b)

A second fraction (500 μl) of homogenate at 20% obtained in (i) is incubated with 500 μl of a buffer comprising 5% sarkosyl (SK5), 5% SDS (SDS5), 1M urea (U1) and proteinase K (PK) at 180 μg/ml (PK6) for 10 min at 37° C., and then steps (iii) and (iv) above are carried out.

II. Western Blotting

The samples obtained are used to perform SDS-PAGE electrophoresis and transferred onto a nitrocellulose membrane under the conditions set out in example 1 and in example 3 of the abovementioned international application WO 99/41280.

Figure 2:
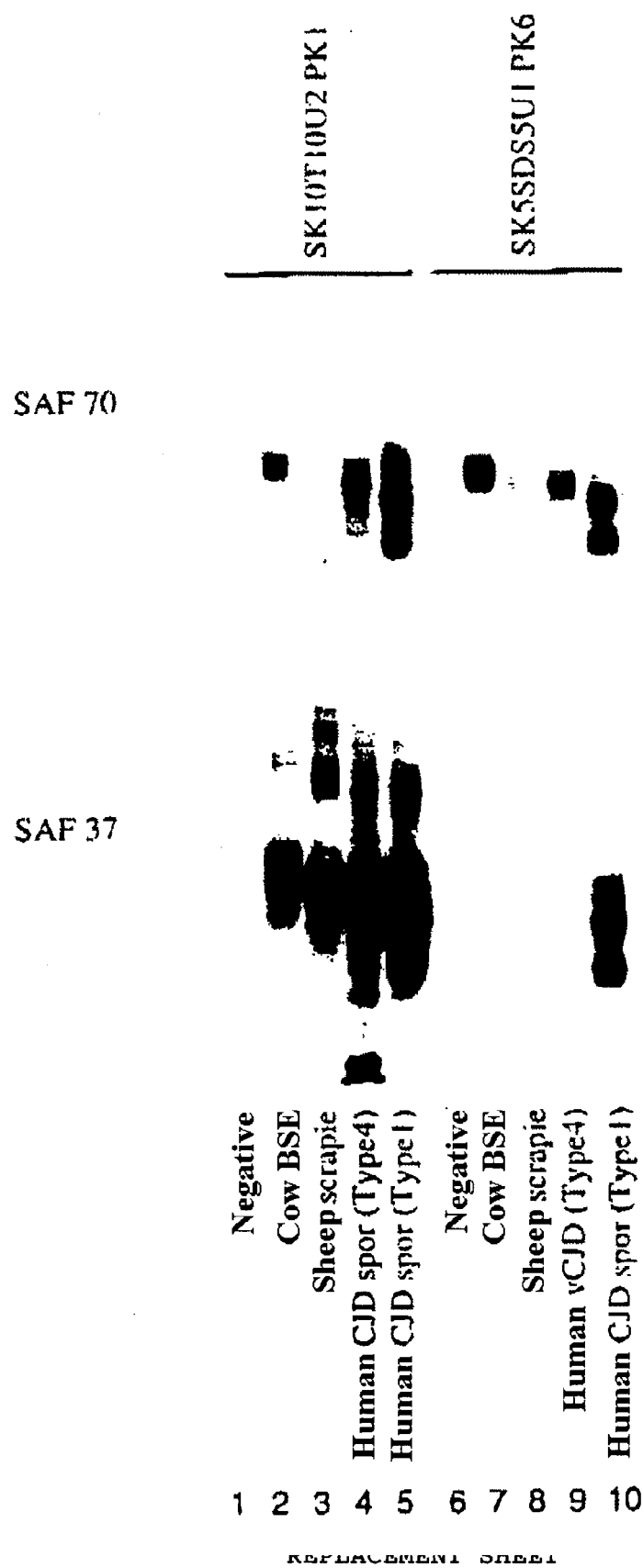
FIG. 2 represents detection of PrP-res by Western blotting.

Immunodetection of the PrP-res is carried out with the monoclonal antibodies SAF70 and SAF37 as described in example 1, above, and peroxidase-conjugated anti-rabbit goat Igs (1/2 500). The immunoreactivity is revealed by chemiluminescence (ECL, Amersham), quantified and visualized on autoradiographic films, as illustrated in FIG. 2.

In this figure:

* lanes 1–5 correspond to conditions according to step (1) or (a) (SK10+T10+U2+PK1).
　lane 1: negative control
　lane 2: cow BSE
　lane 3: sheep scrapie
　lane 4: human vCJD (type 4)
　lane 5: human CJD (type 1) and

* lanes 6–10 correspond to conditions according to step (b) (SK10+SDS5+U1+PK6)
　lane 1: negative control
　lane 2: cow BSE
　lane 3: sheep scrapie
　lane 4: human vCJD (type 4)
　lane 5: human CJD (type 1) and The results obtained show that:

in step (1) or (a) (lanes 1 to 5), the PrP-sen is systematically destroyed, while the signal obtained with the PrP-res is systematically greater, with the antibody directed against the octapeptide motif repeats, to the signal obtained on the same samples with an antibody directed against region 94–230 of the PrP;

in step (b) (lanes 6 to 10), the PrP-sen is systematically destroyed, while the signal obtained in lanes 8 and 10 (in the presence of the antibody directed against the octapeptide motif repeats) is similar to or greater than the signal obtained on the same samples with an antibody directed against region 94–230 of the PrP, whereas it is less and even undetectable on lanes 7 and 9 (PrP-res of BSE).

EXAMPLE 3

Detection of the PrP-res with a Two-Site Immunometric Assay Using, as the Capture Antibody, a Monoclonal Antibody which Recognizes the Octapeptide Motif Repeats To carry out a two-site immunometric assay, the pellet obtained in (iv) in example 2 is, for example, dissolved in a buffer comprising sarkosyl (0.25–1%) and urea (0.25–8 M) or SDS (0.25–1%) and urea (0.25–1 M); the sample obtained will preferably be diluted (to ¼ or to ½), after heating, with a buffer containing albumin, producing a final albumin concentration of between 0.1 and 1% (w/v), or with a buffer containing 1% deoxycholate.

The two-site immunometric assay is performed in microtitration plates containing an antibody which has been immobilized under the conditions already described for other proteins (Grassi et al., 1989). The principle thereof is as follows: the PrP analyzed is recognized by an antibody attached to the solid support (capture antibody) and by a second antibody, which recognizes another part of the molecule, and which is labeled with an enzyme (in this case, acetylcholinesterase, tracer antibody), at 5 Ellman units/ml.

In the context of the invention, the capture antibody is directed against the octapeptide motif repeats and the tracer antibody recognizes a sequence included in region 94–230 of the PrP, for example region 142–160 of the PrP. After washing the solid phase, the enzymatic activity attached to the plate is proportional to the amount of PrP-res having the octapeptide motif repeats initially in the sample analyzed.

In practice, the assay is performed in the following way:

100 μl of the solution of PrP to be analyzed are deposited into the wells of the microtitration plate containing the antibody which recognizes the octapeptide motif repeats. After reaction for 3 hours at room temperature, the plate is washed before adding 100 μl of a solution of the tracer antibody (5 Ellman units/ml). After overnight reaction at +4° C., the plates are washed again before adding 200 μl of a solution of substrate (Ellman reagent, Grassi et al., 1989) which will make it possible to measure the activity of the acetylcholinesterase attached to the solid phase. After 30 minutes of enzymatic reaction, the absorbence (N.D. at 414 nm) of each well is measured.

EXAMPLE 4

Comparative Study of Various Conditions: Step (1) or (a) and Step (b)

Figure 3:
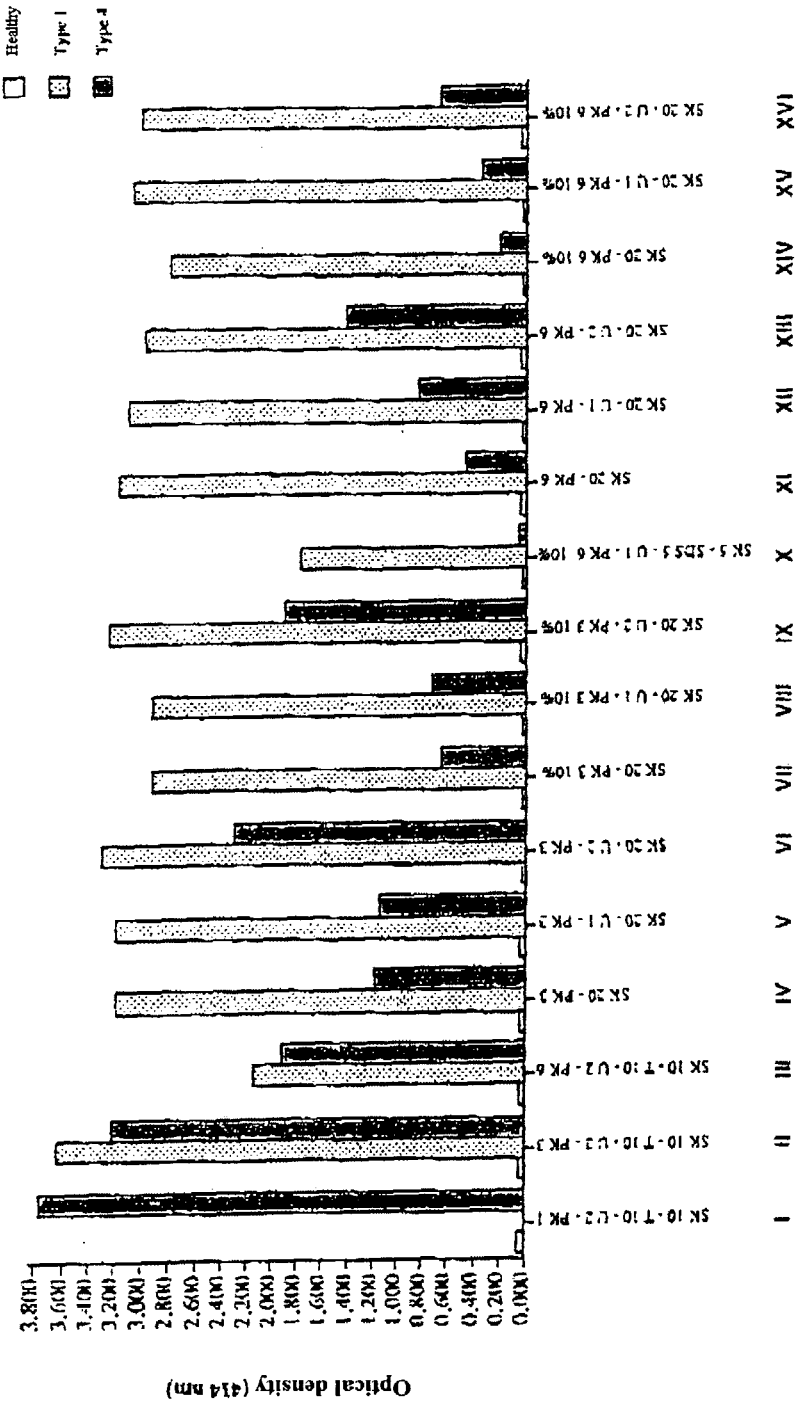
FIGS. 3 to 6 correspond to various conditions according, firstly, to step (1) or (a) and, secondly, to step (b), in humans (FIGS. 3 and 4) and in ruminants (FIGS. 5 and 6), when the presence of the octapeptide motif repeats is detected by a two-site immunometric assay.
Figure 4:
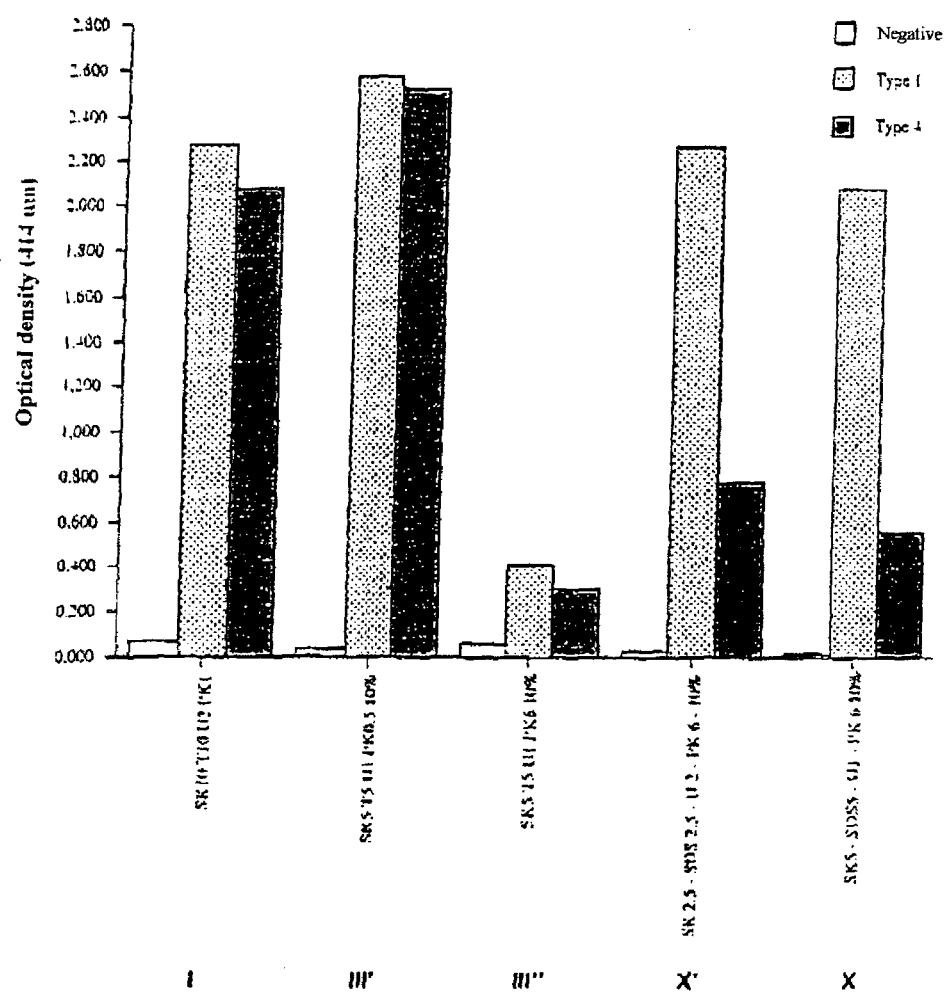

The samples are prepared as described in example 2.
The homogenates are prepared as in example 2.
in humans
FIGS. 3 and 4 illustrate the results obtained with various buffers:
conditions according to step (1) or (a) of the method according to the invention:
　I: homogenate at 20%+SK10+T10+U2+PK1
　III': homogenate at 10%+SK5+T5+U1+PK0.5 (FIG. 4)
conditions according to step (b) of the method according to the invention:
　II: homogenate at 20%+SK10+T10+U2+PK3
　III: homogenate at 20%+SK10+T10+U2+PK6
　III": homogenate at 10%+SK5+T5+U1+PK6 (FIG. 4)
　IV: homogenate at 20%+SK20+PK3
　V: homogenate at 20%+SK20+U1+PK3
　VI: homogenate at 20%+SK20+U2+PK3

VII: homogenate at 10%+SK20+PK3
VIII: homogenate at 10%+SK20+U1+PK3
IX: homogenate at 10%+SK20+U2+PK3
X: homogenate at 10%+SK5+SDS5+U1+PK6
X': homogenate at 10%+SK2.5+SDS2.5+U2+PK6 (FIG. 4)
XI: homogenate at 20%+SK20+PK6
XII: homogenate at 20%+SK20+U1+PK6
XIII: homogenate at 20%+SK20+U2+PK6
XIV: homogenate at 10%+SK20+PK6
XV: homogenate at 10%+SK20+U1+PK6
XVI: homogenate at 10%+SK20+U2+PK6

The amount of PrP-res having conserved the octapeptide motif repeat is measured using the two-site immunometric assay (absorbence or O.D. at 414 nm, see example 3; the appearance of a yellow coloration, Ellman reagent, is measured): negative control (□) sporadic CJD type 1 (□) and vCJD type 4 (■)

in ruminants

Figure 5:
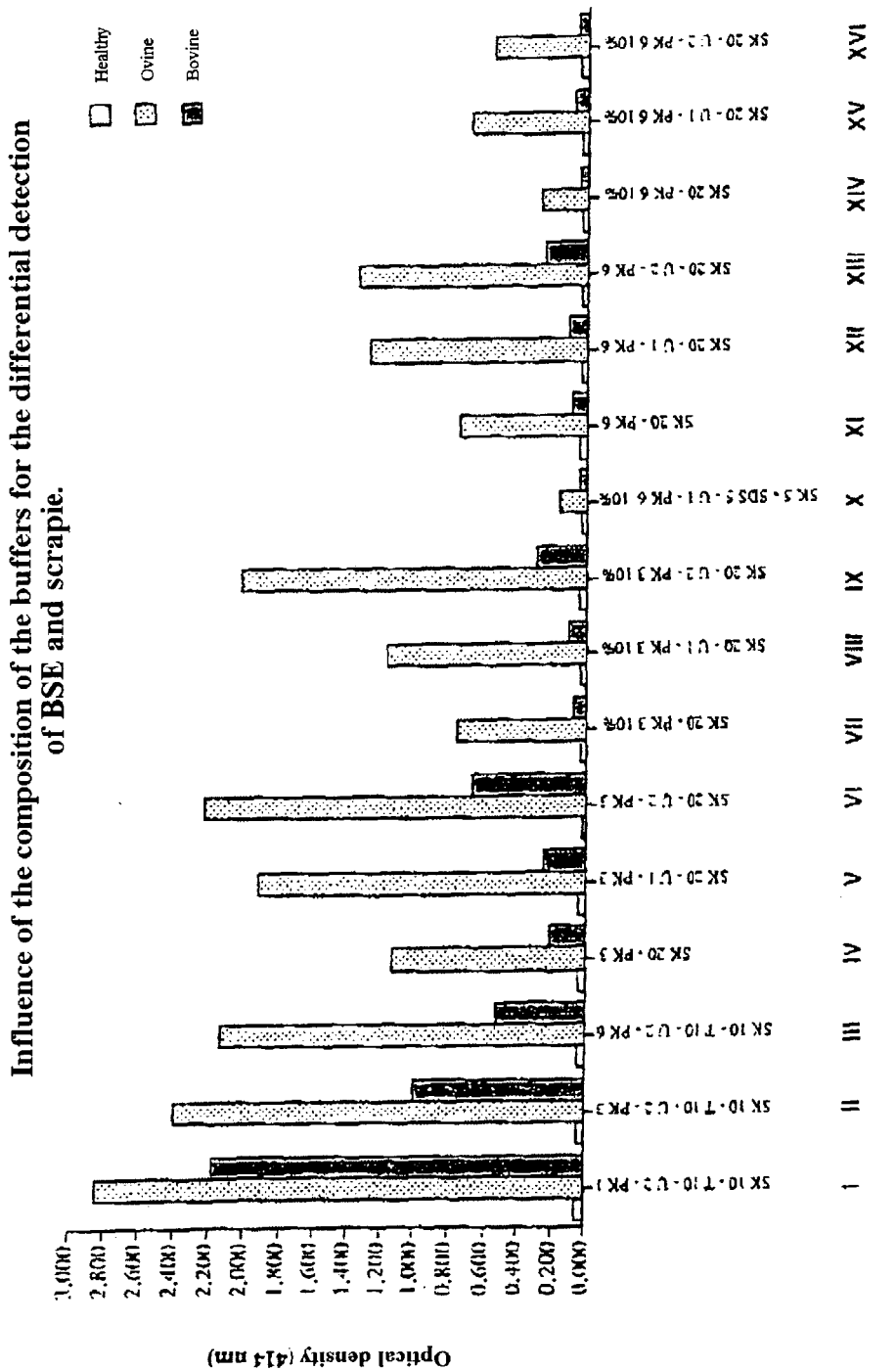
Figure 6:
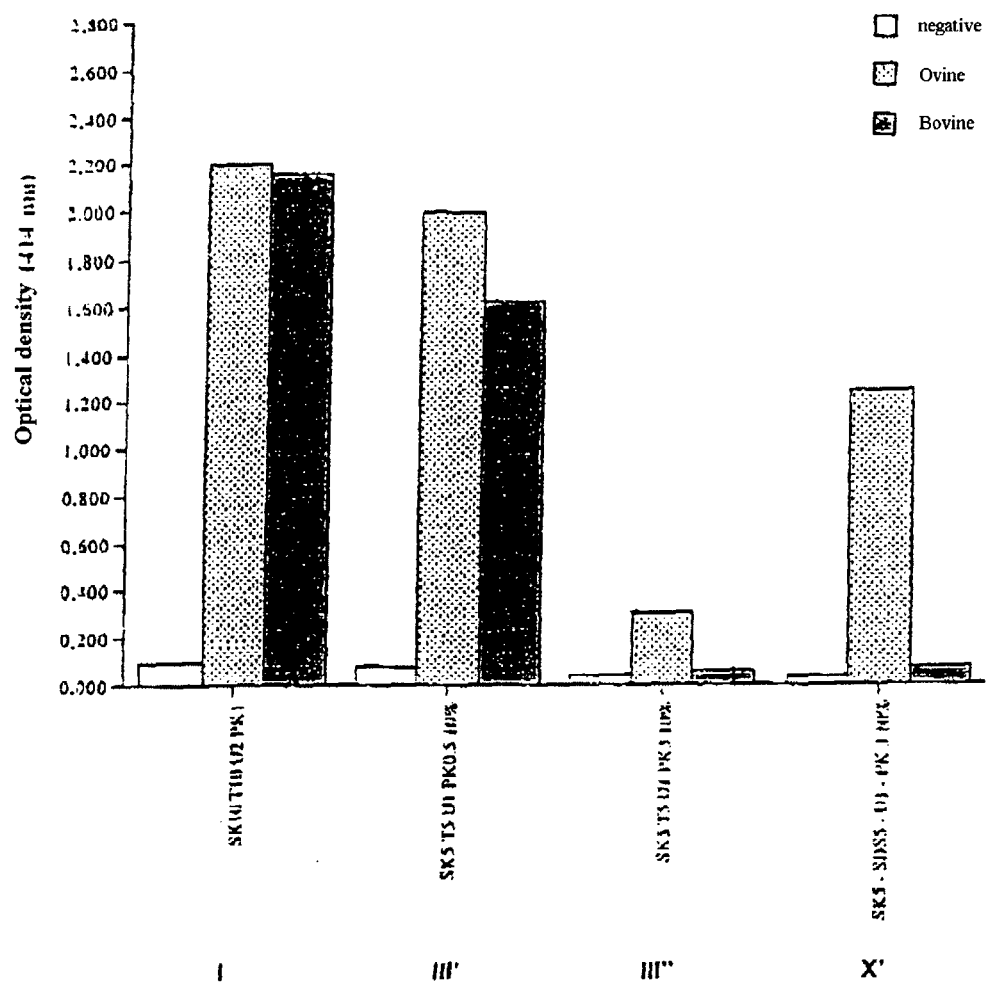

FIGS. 5 and 6 illustrate the results obtained with various buffers:

conditions according to step (1) of the method according to the invention:
I: homogenate at 20%+SK10+T10+U2+PK1
III': homogenate at 10%+SK5+T5+U1+PK0.5 (FIG. 6)
* conditions according to step (4) of the method according to the invention:
II: homogenate at 20%+SK10+T10+U2+PK3
III: homogenate at 20%+SK10+T10+U2+PK6
III": homogenate at 10%+SK5+T5+U1+PK3 (FIG. 6)
IV: homogenate at 20%+SK20+PK3
V: homogenate at 20%+SK20+U1+PK3
VI: homogenate at 20%+SK20+U2+PK3
VII: homogenate at 10%+SK20+PK3
VIII: homogenate at 10%+SK20+U1+PK3
IX: homogenate at 10%+SK20+U2+PK3
X: homogenate at 10%+SK5+SDS5+U1+PK6
X': homogenate at 10%+SK5+SDS5+U1+PK3 (FIG. 5)
XI: homogenate at 20%+SK20+PK6
XII: homogenate at 20%+SK20+U1+PK6
XIII: homogenate at 20%+SK20+U2+PK6
XIV: homogenate at 10%+SK20+PK6
XV: homogenate at 10%+SK20+U1+PK6
XVI: homgenate at 10%+SK20+U2+PK6

The amount of PrP-res having conserved the octapeptide motif repeat is measured using the two-site immunometric assay (absorbence or O.D. at 414 nm, see example 3); negative control (□), bovine UTA (□) and ovine UTA (■).

FIGS. 7 (Western blotting) and 8 (two-site immunometric assay):

The comparison is made using homogenates at 20% of brains from a healthy sheep, from a sheep suffering from scrapie and from a bovine suffering from BSE, obtained under the conditions set out in example 2.

Treatment of the samples:

A: 10% sarkosyl A+10% Triton+2M urea+60 μg/ml proteinase K, 10 minutes

B: 10% sarkosyl+2M urea+240 μg/ml proteinase K, 10 minutes

C: 10% sarkosyl+240 μg/ml proteinase K, 10 minutes

Detection by Western blotting (FIG. 7): antibodies Saf37 and Saf84 (see example 1);

by immunometric analysis (FIG. 8): capture with Saf37 and revelation with an antibody directed against region 94–230 of the PrP.

FIGS. 9 (Western blotting) and 10 (two-site immunometric assay):

The comparison is made using homogenates at 20% of brains from a healthy sheep, from a sheep suffering from scrapie and from a bovine suffering from BSE, obtained under the conditions set out in example 2.

Treatment of the samples:

A: 10% sarkosyl+10% Triton+2M urea+60 μg/ml proteinase K, 10 minutes

B: 10% SDS+5% Triton+2M urea+180 μg/ml proteinase K, 10 minutes

Detection under the same conditions as above.

Increasing only the dose of PK makes it possible to reveal a differential sensitivity of the region of octapeptide motif repeats between BSE and scrapie in sheep but not in humans (between type 1 and type 4).

On the other hand, by also modifying the composition of surfactant and of chaotropic agent, this makes it possible to reveal a differential sensitivity of the region of octapeptide motif repeats in all cases.

EXAMPLE 5

Influence of the Composition of the Buffers on the Differential Detection of BSE and Scrapie FIGS. 11 (Western blotting) and 12 (two-site immunometric assay):

The comparison is made using homogenates at 10% of brains from healthy mice or from mice experimentally infected with the C506M3 strain (scrapie) or with a 6PBI strain (BSE), obtained under conditions set out in example 2.

Treatment of the samples:

A: 10% sarkosyl+10% Triton+2M urea+30 μg/ml proteinase K, 10 minutes

B: 10% sarkosyl+10% Triton+2M urea+60 μg/ml proteinase K, 10 minutes

C: 10% sarkosyl+10% Triton+2M urea+180 μg/ml proteinase K, 10 minutes

D: 10% sarkosyl+10% Triton+2M urea+360 μg/ml proteinase K, 10 minutes

E: 10% sarkosyl+2M urea+180 μg/ml proteinase K, 10 minutes.

Detection by Western blotting (FIG. 11): antibodies Saf37 and Saf70 (see example 1);

by immunometric analysis (FIG. 12): capture with Saf37 and revelation with an antibody directed against region 94–230 of the PrP.

The results obtained show that increasing only the dose of PK makes it possible to reveal a differential sensitivity of the region of octapeptide motif repeats between BSE and scrapie, in mice.

EXAMPLE 6

Figure 13:
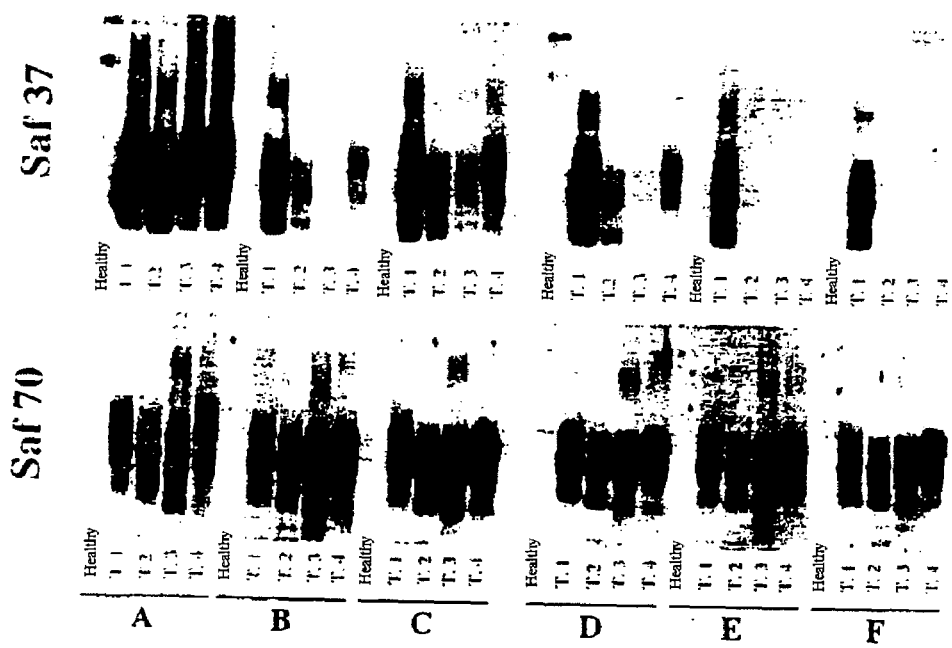
FIGS. 13 and 14 illustrate the influence of the composition of the buffers and of the concentration of proteinase K (PK) for detecting the various types of CJD.

Influence of the Buffers and of the Proteinase K Concentration on the Detection of the Various CJDs FIGS. 13 (Western blotting) and 14 (two-site immunometric assay):

The comparison is made using homogenates at 10% of brains from healthy humans and from humans suffering from CJD (types 1, 2, 3 and 4), obtained under the conditions set out in example 2.

Treatment of the samples:

A: 10% sarkosyl+10% Triton+2M urea+30 µg/ml proteinase K, 10 minutes

B: 10% sarkosyl+10% Triton+2M urea+180 µg/ml proteinase K, 10 minutes

C: 10% sarkosyl+30 µg/ml proteinase K, 10 minutes

D: 10% sarkosyl+60 µg/ml proteinase K, 10 minutes

E: 10% sarkosyl+180 µg/ml proteinase K, 10 minutes

F: 10% sarkosyl+360 µg/ml proteinase K, 10 minutes.

Figure 14:
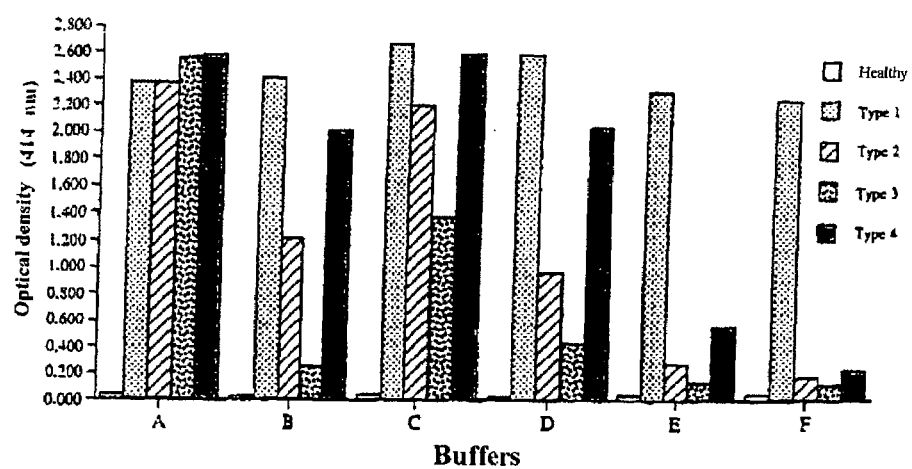

Detection by Western blotting (FIG. 13): antibodies Saf37 and Saf70 (see example 1);

by immunometric analysis (FIG. 14): capture with Saf37 and revelation with an antibody directed against region 94–230 of the PrP.

FIGS. 15 (Western blotting) and 16 (immunometric analysis)

The comparison is made using homogenates at 10% of brains from healthy humans and from humans suffering from CJD (types 1, 2, 3 and 4), obtained under the conditions set out in example 2.

Treatment of the samples:

FIG. 15: digestion with proteinase K (150 µg/ml), 10 minutes.

FIG. 16: 10% sarkosyl+2M urea+proteinase K (from 30 to 360 µg/ml), for 10 minutes.

Detection by Western blotting (FIG. 15): antibody Saf37 and an antibody directed against region 94–230 of the PrP (see example 1);

by immunometric analysis (FIG. 16): capture with Saf37 and revelation with an antibody directed against region 94–230 of the PrP.

The results obtained show that increasing the dose of PK makes it possible to reveal a differential sensitivity of the region of octapeptide motif repeats in the various types of CJD. Under these conditions, no significant difference exists between type 1 and type 4; changing the composition of surfactant and of chaotropic agent, at the same dose of PK (E, FIGS. 13 and 14), makes it possible to destroy the octapeptides in type 4 while at the same time conserving them in type 1.

In addition, FIG. 16 makes it possible to show the difference in sensitivity of the PrPs-res derived from various strains, for the same buffer, as a function of the dose of PK.

Moreover, FIG. 15 shows that direct treatment of the homogenate with PK reveals another type of sensitivity of the PrP-res to degradation.

EXAMPLE 7

Detection by Western Blotting of Digested PrP-res Purified in SAF Form

Homogenates, obtained under the conditions according to example 2, are treated as follows:

20% homogenate (500 µl)+20% NaCl (500 µl)+[20% sarkosyl+2% SB314] (500 µl)+PK (20 µg/ml final concentration) for 1 hour.

Figure 17:
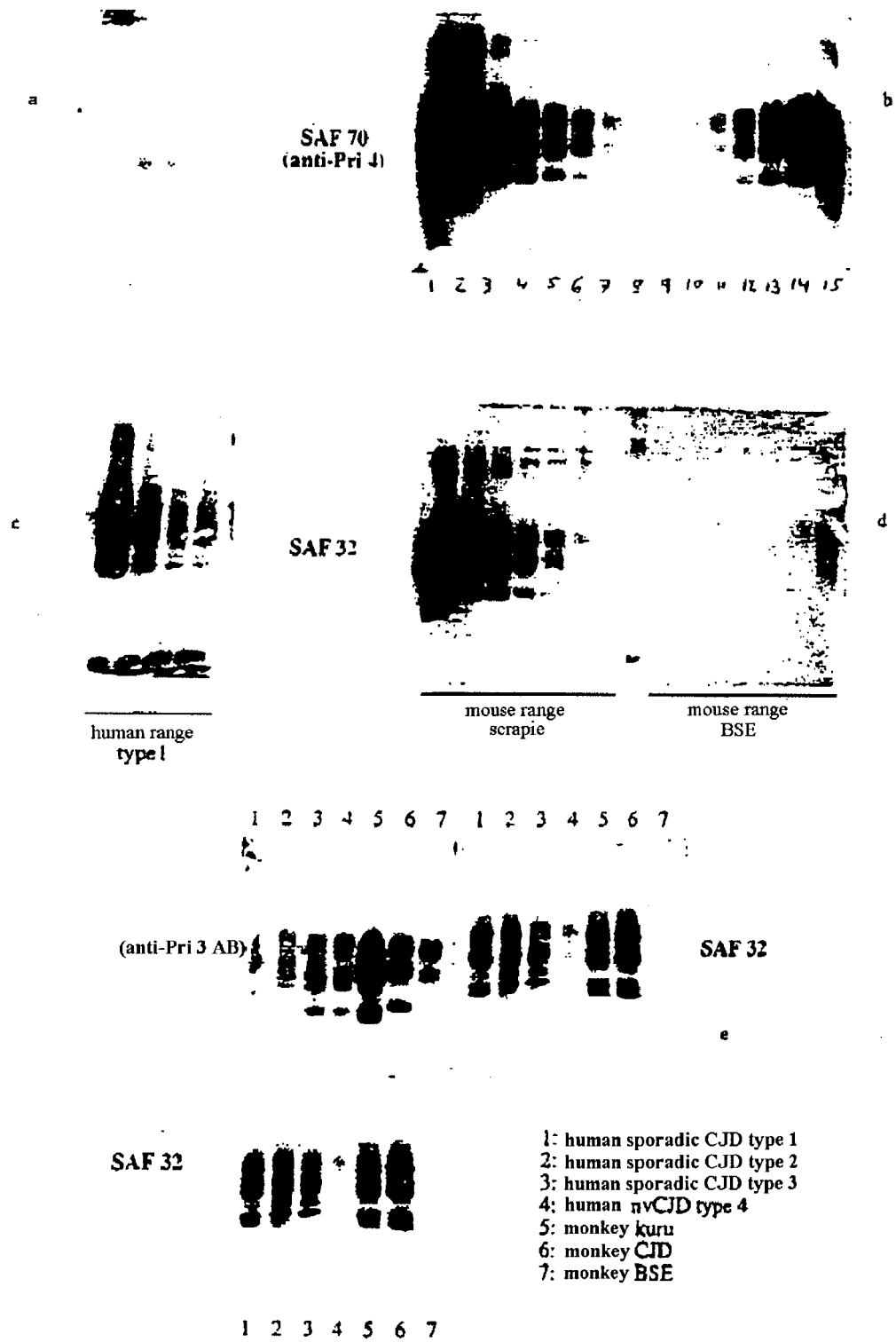
FIG. 17 illustrates the detection, by Western blotting, of PrP-res digested with PK and purified in SAF form.

FIG. 17 illustrates the results:

b and d:

lanes 1–7: results obtained with various dilutions of scrapie strain C506M3 in mice (dilutions 1/20, 1/50, 1/250, 1/500, 1/1 000 and 1/2 000)

lane 8: molecular weights lanes 9–15: results obtained with various dilutions of BSE strain in mice (dilutions of 1/1 000 to 1/10).

It is possible to entirely eliminate the BSE signal.

a and c: the results obtained confirm that there is a significant increase in the signal in the presence of antibodies directed against the octapeptide motif repeats.

e: this figure shows that it is possible to obtain a decrease in the signal with BSE, both in monkeys and in humans (lanes 4 and 7)

REFERENCES

Butler D., *Nature*, 1998, 395, 6–7.

Collinge J. et al., *Nature*, 1996, 393, 685–690.

Créminon, C. et al., *J. Immunol. Methods*, 1993, 162, 179–192.

Ellman, G. et al., *Biochem. Pharmacol.*, 1961, 7, 88–95.

Frobert, Y et al., *Methods Mol. Biol.*, 1991, 80, 57–68.

Grassi, J. et al., *Anal. Biochem.*, 1988, 168, 436–450.

Grassi J. et al., *J. Immunol. Methods*, 1989, 123, 193–210.

Grathwohl K. U. et al., *J. Virol. Methods*, 1997, 64, 205–216.

Kuczius T. et al., *Mol. Med.*, 1999, 5, 406–418.

Lasmezas C. et al., *Nature*, 1996, 381, 743–744.

Lasmezas C. et al., *Science*, 1997, 275, 402–405.

McLaughlin L. L. et al., *Biochem. Biophys. Res. Comm.*, 1987, 144, 469–476.

Oesch B. et al., *Curr. Topics Microbiol. and Immunol.*, 1991, 172, 109–124

Oesch B. et al., *Biochemistry*, 1994, 33, 5926–5931.

Parchi P. et al., *Nature*, 1997, 386, 232–234.

Priola S. A., *Nature Med.*, 1996, 2, 12, 1303–1304.

Prusiner S. B. et al., *Cell*, 1984, 38, 127–134.

Safar J. et al., *Nature Med.*, 1988, 10, 1157–1165.

Schaller O. et al. *Acta Neuropathol.* 1999, 98, 437–443.

Serban D. et al., *Neurology*, 1990, 40, 110.

As emerges from the above, the invention is in no way limited to its methods of implementation, preparation and application which have just been described more explicitly; on the contrary, it encompasses all the variants thereof which may occur to a person skilled in the art, without departing from the context or scope of the present invention.

What is claimed is:

1. A method for diagnosing a TSSE (transmissible spongiform subacute encephalopathy) or a prion disease caused by a UTA strain comprising:

(1) treating a sample suspected of containing a prion with proteinase K for a time and under conditions that completely degrade normal prion protein (Prp-sen), but which only partially digest abnormal prion protein (PrP-res) so that all or some of the octapeptide motif repeats comprising P(H/Q)GGG(-/T)WGQ (SEQ ID NO: 1) in the abnormal prion protein (Prp-res) are retained, (2) contacting said sample from (1) with a ligand which binds to said octapeptide motifs for a time and under conditions sufficient for complex formation between said ligand and polypeptides containing said octapeptide motif, and (3) detecting complex formation, wherein complex formation is indicative of the presence of TSSE or a prion disease.

2. The method of claim 1, wherein (1) proteinase K treatment is carried out for a period ranging from 30 seconds to 2 hours at a temperature of less than 80° C.

3. The method of claim 1, wherein (1) proteinase K treatment is carried out for a period ranging from 10 minutes and 30 minutes.

4. The method of claim 1, wherein the sample is brain tissue and (1) proteinase K treatment is carried out with a concentration of proteinase K ranging from 30 μg/ml to 200 μg/ml for 10 mins at 37° C. for a 10% brain tissue homogenate, or for a period and at a concentration of the brain tissue homogenate equivalent to treatment of a 10% brain tissue homogenate with proteinase K at a concentration ranging from 30 μg/ml to 200 μg/ml for 10 mins at 37° C.

5. The method of claim 1, wherein step (1) proteinase K treatment is carried out at a concentration of proteinase K ranging from 10 μg/ml to 70 μg/ml for 30 minutes at 37° C. of a 10% homogenate of the sample.

6. The method of claim 1, wherein the proteinase K is dissolved in a biological sample homogenization buffer.

7. The method of claim 1, wherein the proteinase K is dissolved in a buffer comprising at least one surfactant, at least one chaotropic agent and/or at least one salt.

8. The method of claim 1, wherein the proteinase K is dissolved in a buffer comprising at least one anionic surfactant selected from the group consisting of SDS (sodium dodecyl sulfate), sarkosyl (lauroylsarcosine), sodium cholate, sodium deoxycholate and sodium taurocholate.

9. The method of claim 1, wherein the proteinase K is dissolved in a buffer comprising at least one zwitterionic surfactant selected from the group consisting of SB 3-10 (decylsulfobetaine), SB 3-12 (dodecylsulfobetaine), SB 3-14 tetradecylsulfobetaine), SB 3-16 (hexadecylsulfobetaine), CHAPS and deoxy-CHAPS.

10. The method of claim 1, wherein the proteinase K is dissolved in a buffer comprising at least one nonionic surfactant selected from the group consisting of C12E8 (dodecyl-octaethylene glycol), Triton X100, Triton X114, Tween 20, Tween 80, MEGA 9 (nonanoylmethylglucamine), octylglucoside, LDAO (dodecyldimethylamine oxide) and NP40 (nonylphenylpolyethyleneglycol).

11. The method of claim 1, wherein the proteinase K is dissolved in a buffer comprising a mixture of two or more ionic, zwitterionic and/or nonionic surfactants.

12. The method of claim 1, wherein the proteinase K is dissolved in a buffer comprising at least one chaotropic agent selected from the group consisting of urea and guanidine, or a mixture thereof.

13. The method of claim 1, wherein the proteinase K is dissolved in a buffer comprising at least one metal or alkali metal salt, or mixtures thereof.

14. The method of claim 1, wherein the proteinase K is dissolved in a buffer comprising at least 5% of an anionic surfactant.

15. The method of claim 1, wherein the proteinase K is dissolved in a buffer comprising at least 5% of sarkosyl, optionally combined with SDS.

16. The method of claim 1, wherein said ligand is an antibody that specifically binds to said octapeptide motif.

17. The method of claim 1, wherein said ligand is a monoclonal antibody that specifically binds to said octapeptide motif.

18. The method of claim 1, wherein said ligand is an aptamer that specifically binds to said octapeptide motif.

* * * * *

SEQUENCE LISTING

<160> NUMBER OF SEQ ID NOS: 2

<210> SEQ ID NO 1
<211> LENGTH: 9
<212> TYPE: PRT
<213> ORGANISM: Artificial
<220> FEATURE:
<223> OTHER INFORMATION: Octapeptide motif common to hamster, human, bovine and ovine PrP-sen. The octapeptide motif corresponds to amino acids 51-91 of the human PrP sequence.
<220> FEATURE:
<221> NAME/KEY: MISC_FEATURE
<222> LOCATION: (2)..(2)
<223> OTHER INFORMATION: X at position 2 is H or Q
<220> FEATURE:
<221> NAME/KEY: MISC_FEATURE
<222> LOCATION: (6)..(6)
<223> OTHER INFORMATION: X at position 6 is either absent or T

<400> SEQUENCE: 1

Pro Xaa Gly Gly Gly Xaa Trp Gly Gln
1               5

<210> SEQ ID NO 2
<211> LENGTH: 14
<212> TYPE: PRT
<213> ORGANISM: Artificial
<220> FEATURE:
<223> OTHER INFORMATION: Synthetic peptide representative of the PrP octapeptide motif repeat corresponding to the sequence of residues 79-92 of human PrP.

<400> SEQUENCE: 2

Gly Gly Trp Gly Gln Pro His Gly Gly Gly Trp Gly Gln Gly
1               5                   10